(12) United States Patent
Salo

(10) Patent No.: US 8,456,627 B2
(45) Date of Patent: Jun. 4, 2013

(54) STRUCTURE OF MEASUREMENT WINDOW

(75) Inventor: Harri Salo, Vantaa (FI)

(73) Assignee: Janesko Oy, Vantaa (FI)

( * ) Notice: Subject to any disclaimer, the term of this patent is extended or adjusted under 35 U.S.C. 154(b) by 217 days.

(21) Appl. No.: 12/892,415

(22) Filed: Sep. 28, 2010

(65) Prior Publication Data

US 2011/0075141 A1 Mar. 31, 2011

(30) Foreign Application Priority Data

Sep. 29, 2009 (FI) .................................... 20095992

(51) Int. Cl.
*G01N 21/01* (2006.01)

(52) U.S. Cl.
CPC ...................................... *G01N 21/01* (2013.01)
USPC ......................................................... 356/244

(58) Field of Classification Search
CPC ...................................................... G01N 21/01
USPC ................................................. 356/244–246
See application file for complete search history.

(56) References Cited

U.S. PATENT DOCUMENTS

| | | | |
|---|---|---|---|
| 4,713,552 A | 12/1987 | Denis et al. | |
| 4,829,186 A | 5/1989 | McLachlan et al. | |
| 5,773,825 A | 6/1998 | Doyle | |
| 6,067,151 A | 5/2000 | Salo | |
| 6,118,520 A | 9/2000 | Harner | |
| 6,760,098 B2 | 7/2004 | Salo | |
| 7,619,723 B2 | 11/2009 | Salo | |
| 2004/0122280 A1* | 6/2004 | Forney | .............................. 600/2 |

FOREIGN PATENT DOCUMENTS

| | | | |
|---|---|---|---|
| DE | 4414975 A1 | 11/1995 |
| DE | 4418180 A1 | 1/1996 |
| FI | 108259 B | 12/2001 |
| FI | 113566 B | 5/2004 |
| FI | 118864 B | 4/2008 |

OTHER PUBLICATIONS

*Finnish Search Report issued on May 11, 2010, by Finnish Patent Office for Finnish Application No. 20095992.

* cited by examiner

*Primary Examiner* — Michael P Stafira
(74) *Attorney, Agent, or Firm* — Buchanan Ingersoll & Rooney PC

(57) ABSTRACT

A measurement window structure is disclosed for an optical process measurement device. The measurement window structure can include a measurement window made of an optical material and having a measurement surface that is arranged to be placed into a process solution, a sealing surface formed to a frame structure of the optical process measurement device and facing the process solution, the measurement window made of an optical material being arranged to press against the sealing surface, and an attaching device or mechanism for pressing the measurement window made of an optical material against the sealing surface and for attaching it to the frame structure. The sealing surface formed to the frame structure can be a rotationally symmetrical surface and the surface pressing against the sealing surface formed to the frame structure of the measurement window made of an optical material can be a rotationally symmetrical surface.

9 Claims, 4 Drawing Sheets

STRUCTURE OF MEASUREMENT WINDOW

RELATED APPLICATION

This application claims priority under 35 U.S.C. §119 to Finnish Patent Application No. 20095992 filed in Finland on Sep. 29, 2009, the entire content of which is hereby incorporated by reference in its entirety.

FIELD

A measurement window structure is disclosed for an optical process measurement device.

BACKGROUND INFORMATION

A reliable optical process measurement device should withstand occasional high pressures, such as 100 bars, in oil refinery applications or in separation processes used in food industry. An example to be mentioned of such optical measurement devices is a refractometer.

A measurement window or a prism made of an optical material can be installed from the inside of the device, its pressure resistance being thus restricted to pressures below 50 bars. An example of this type of implementation is the process refractometer PR-03 of K-Patents Oy or FI Patent Publication 108259.

An alternative is to install the prism to the process side, as for example in refractometers PR-01 of K-Patents Oy. Due to the prism geometry, the refractometer PR-01 includes two small process seals. Small process seals and sealing grooves are technically difficult to manufacture because of tolerances, for example. Moreover, installation of small seals is laborious for persons installing instrumentation, and includes precision and due to two separate seals the construction is not hygienic.

Further examples of process refractometers that can be mentioned and solutions used in connection with them are the structures disclosed in FI publications 113566 and 118864.

SUMMARY

A measurement window structure for an optical process measurement device is disclosed, the measurement window structure comprising: a measurement window made of an optical material and having a measurement surface that is configured for placement into a process solution; a sealing surface for a frame structure of the optical process measurement device for facing the process solution, the measurement window being arranged to press against the sealing surface; and attaching means for pressing the measurement window against the sealing surface to attach the measurement window to the frame structure, the sealing surface being a rotationally symmetrical surface and the surface pressing against the sealing surface being a rotationally symmetrical surface, the surface of the measurement window being provided with at least one planar surface through which light will be guided or reflected to the measurement surface, and the sealing surface being at least partly provided with an opening through which light will be guided to the planar surface.

An optical process measurement device is disclosed comprising: a measurement window made of an optical material and having a measurement surface that is configured for placement into a process solution; a sealing surface for a frame structure of the optical process measurement device for facing the process solution, the measurement window being arranged to press against the sealing surface; and attaching means for pressing the measurement window against the sealing surface to attach the measurement window to the frame structure, the sealing surface being a rotationally symmetrical surface and the surface pressing against the sealing surface being a rotationally symmetrical surface, the surface of the measurement window being provided with at least one planar surface through which light will be guided or reflected to the measurement surface, and the sealing surface being at least partly provided with an opening through which light will be guided to the planar surface.

BRIEF DESCRIPTION OF THE DRAWINGS

In the following, features disclosed herein will be described in greater detail with reference to an exemplary embodiment illustrated in the accompanying drawings, in which.

DETAILED DESCRIPTION

An exemplary measurement window structure as disclosed herein includes a measurement window made of an optical material and having a measurement surface that is arranged to be placed into a process solution. A sealing surface can be formed to a frame structure of the optical process measurement device and facing the process solution. The measurement window can be made of an optical material arranged to press against the sealing surface. Attaching means can be provided for pressing the measurement window made of an optical material against the sealing surface and for attaching it to the frame structure.

The exemplary sealing surface can be formed to the frame structure with a rotationally symmetrical surface. The surface pressing against the sealing surface formed to the frame structure of the measurement window and made of an optical material can be a rotationally symmetrical surface.

According to exemplary embodiments, a measurement window made of an optical material is installed from the process side, the maximum process pressure being thus determined, for example, only by the process seal. In other words, the pressure prevailing in an exemplary process does not tend to open the sealing but presses the measurement window made of an optical material tightly against the sealing surface in the frame structure. The sealing surfaces and the seal of the measurement window structure do not require particular precision of manufacture, and the seal can be easy to install. A construction with a single process seal can be easy to make hygienic.

Exemplary embodiments can provide an affordable means for obtaining a measurement window that stays clean, and avoids contamination of the measurement surface. If substance to be measured attaches to the measurement surface and the liquid no longer changes, the measurement ceases to function in a desired manner. The measurement window structure disclosed herein can allow a measurement window to be produced, depending on the measurement geometry, in the form of a protrusion in relation to other process surfaces of the measurement device. A protruding construction can provide a better rate of change of the sample and the self-cleaning ability of the construction in process conditions where there is flow in relation to a construction in which the measurement window is flush with the other process surfaces or even in a recess. The structure disclosed herein can allow an optical measurement device to be provided with a much better capacity for remaining clean than known constructions.

Figure 1:
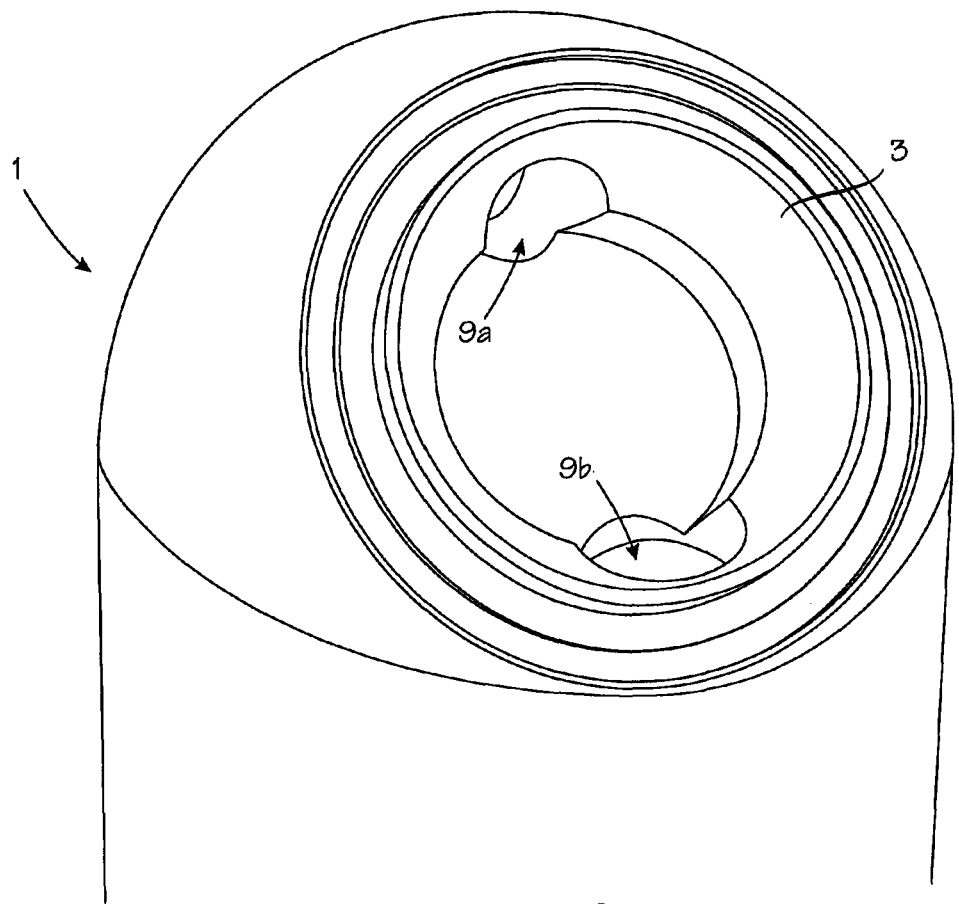
FIG. 1 is a schematic view of a tip part of a frame structure of an exemplary optical process measurement device without a measurement window made of an optical material.
Figure 2:
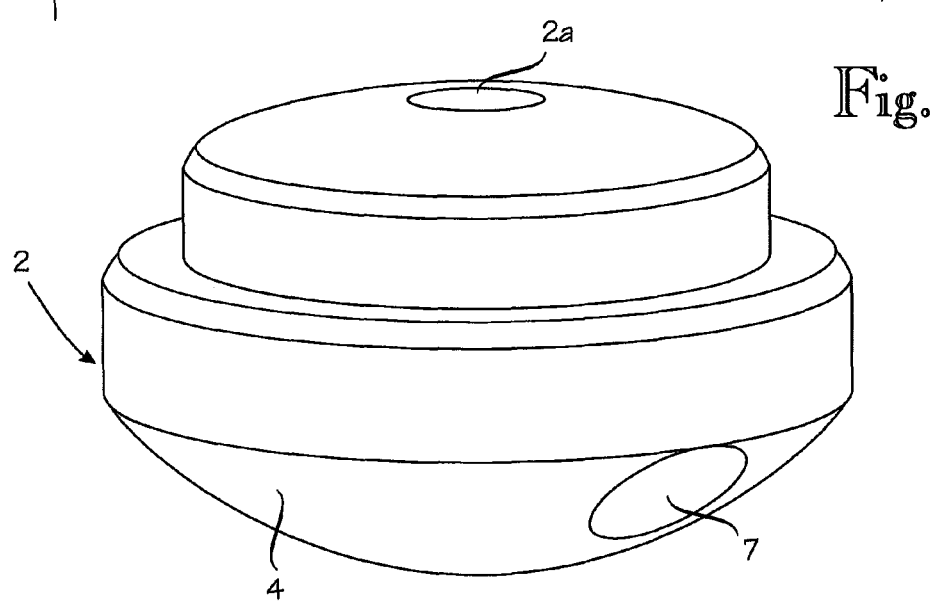
FIG. 2 is a schematic view of an exemplary measurement window made of an optical material for the optical process measurement device.
Figure 3:
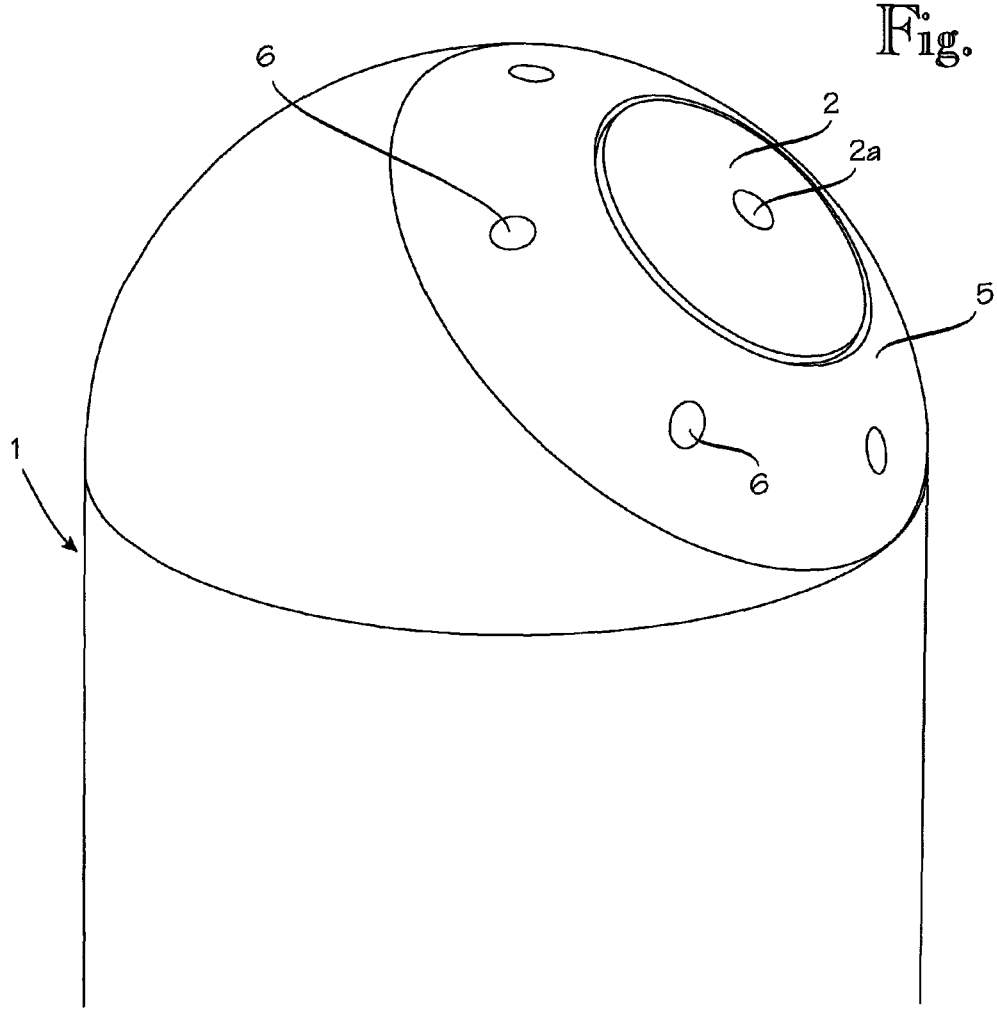
FIG. 3 is a schematic view of the tip part of the frame structure of an exemplary optical process measurement device, with the measurement window made of an optical material attached to the tip.
Figure 4:
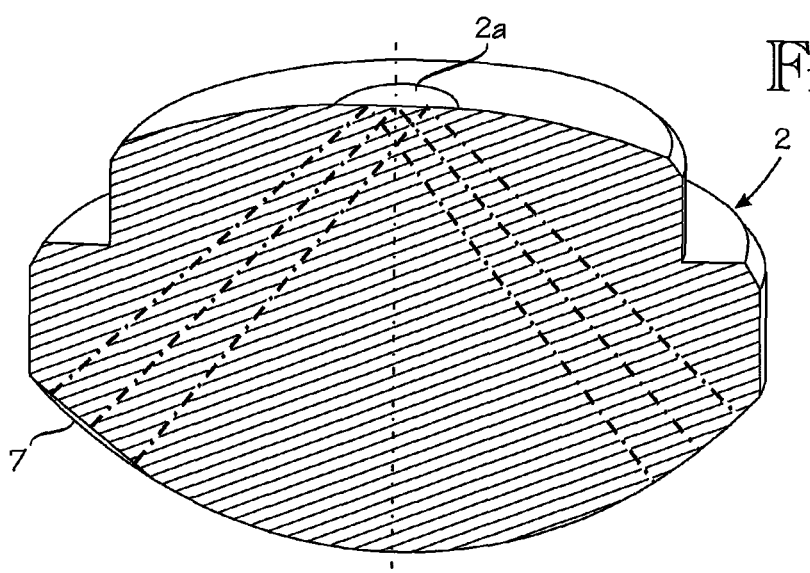
FIG. 4 is a schematic sectional view of an exemplary measurement window made of an optical material, with supply and reflection of light schematically marked therein.
Figure 5:
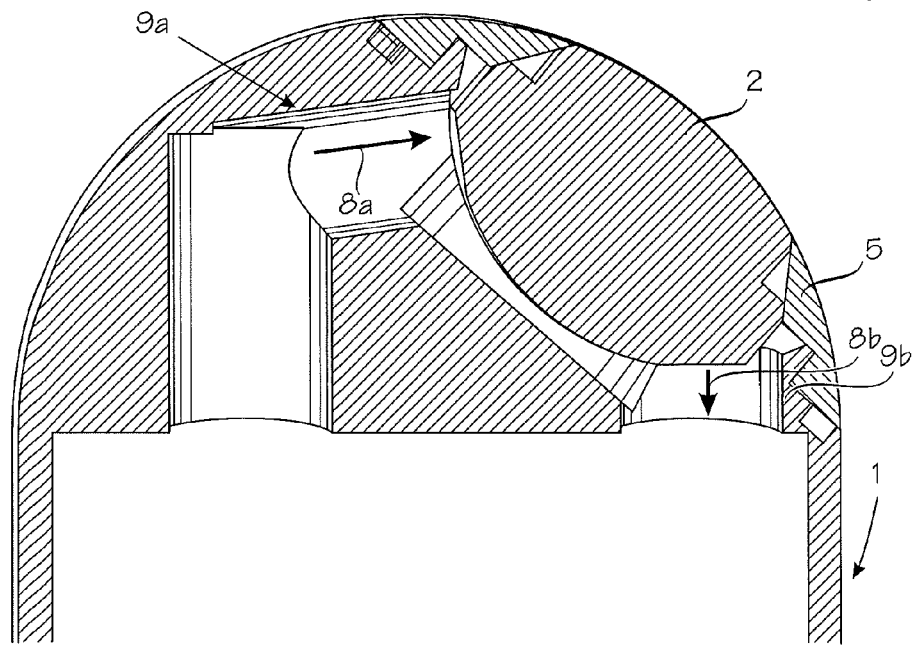
FIG. 5 is a schematic sectional view of the tip part of an exemplary optical process measurement device with the measurement window made of an optical material attached to the tip.
Figure 6:
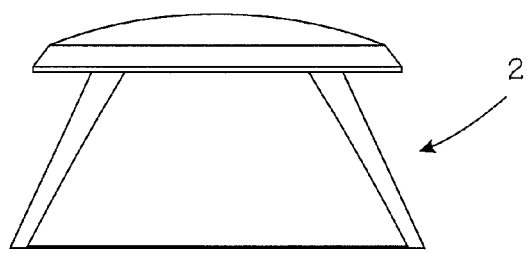
FIGS. 6 to 10 are schematic views taken from different directions of a second exemplary embodiment of a measurement window made of an optical material for the measurement window structure disclosed herein.
Figure 7:
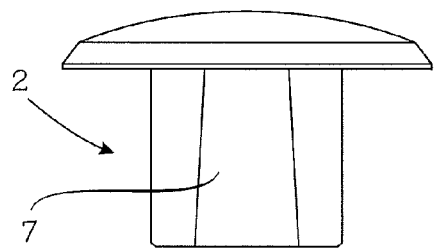
Figure 8:
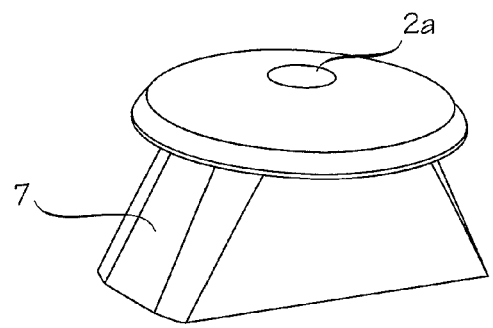
Figure 9:
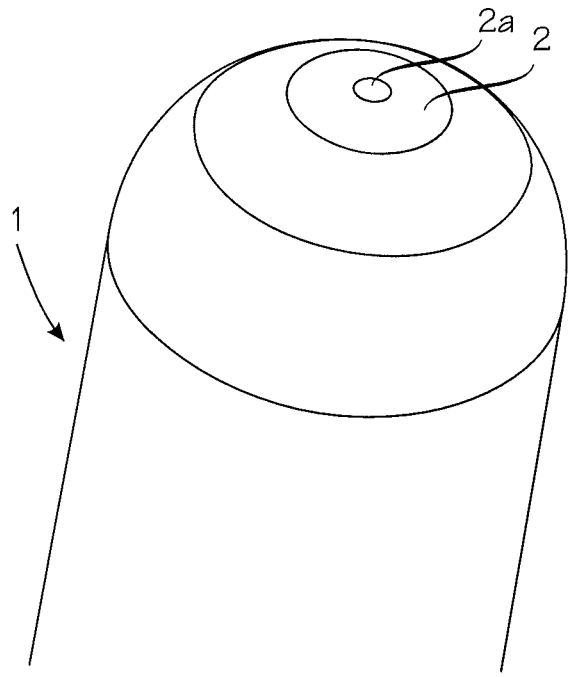

FIG. 1 is a schematic view of a tip part 1 of a frame structure of an exemplary optical process measurement device, without a measurement window made of an optical material. A measurement window 2 made of an optical material is in turn shown in FIG. 2. FIGS. 3 and 5 show the tip part 1 of the optical process measurement window with the measurement window 2 made of an optical material attached thereto. FIG. 4 is a schematic view of light travelling in the measurement window 2 made of an optical material. FIG. 1 also shows openings 9a, 9b through which a bundle of light beams is guided to the measurement window 2 made of an optical material and further on for analysis.

The details shown in FIGS. 1 to 5 relate to an exemplary process refractometer. The figures only show a part of the refractometer frame structure, i.e. the tip part, whereto the measurement window made of an optical material is attached. The measurement window made of an optical material can be brought into contact with the process liquid to be measured. The measurement takes place by measuring the refractive index of the process solution through total reflection created at the interface between the measurement window made of an optical material and the solution. For this purpose the interface is subjected to a bundle of light beams that reflects from the interface according to the basic principle disclosed in FIG. 4. Part of the bundle of beams is reflected from the solution completely, while part of it is partly absorbed into the solution. This creates an image where the location of the boundary between a bright area and a dark area depends on the critical angle and thus on the refractive index of the process solution. An aspect of refraction measurement is the analysis of the image created by the reflection of light. The purpose of this image analysis is to find the critical angle (i.e., the limit), where the bright area of the image created in the above manner changes into a dark area. The bundle of light beams may be guided to the interface either through the measurement window made of an optical material or from the side of the liquid to be measured. The light source and the means used in the image analysis have been placed inside the refractometer frame structure. This has not been shown in the figures, because it is known technology for a person skilled in the art. In this connection we refer to FI patent publications 108259, 113566 and 118864 mentioned earlier, in which such details have been described in greater detail, and which disclosures are incorporated herein in their entireties by reference.

The operating principle of a refractometer has been known for more than hundred years. Food industry, wood processing industry, chemical industry and different research areas in general serve as exemplary fields of application for refractometers.

When a refractometer measurement is carried out, a structure according to FIG. 3, for example, is taken into the process solution to be measured so that the measurement window 2 made of an optical material is in contact with the process liquid to be measured. The process liquid to be measured may be under high pressure, as stated previously. Hence the measurement window structure should withstand high pressures and, moreover, the structure should be easy to realize.

In FIG. 1 reference numeral 3 indicates a sealing surface made to the frame structure of the optical process measurement device and facing the process solution. In the structure of the disclosure the measurement window made of an optical material is installed from the process side and thus the sealing surface 3 formed to the frame structure is the surface facing the process solution during measurement.

According to an exemplary aspect disclosed herein, the sealing surface 3 formed to the frame structure 1 is rotationally symmetrical surface. Correspondingly, a surface 4 pressing against the sealing surface 3 formed to the frame structure of the measurement window 2 made of an optical material is a rotationally symmetrical surface. The surface 4 is clearly seen in FIG. 2, which shows the measurement window 2 made of an optical material. FIG. 2 further shows that the sealing surface 4 of the measurement window 2 made of an optical material is a surface equal in size with the largest dimension of the measurement window. Hence, an exemplary solution with regard to pressure resistance is obtained. The process solution pressure presses the measurement window made of an optical material tightly against the frame structure. The counter surface pair formed by the surfaces 3 and 4 can be large, thus creating a solution that withstands pressure well.

The measurement window 2 made of an optical material is attached in place with attaching members 5, 6 as shown in FIG. 3, for example.

The measurement window 2 made of an optical material may be advantageously manufactured as a rotationally symmetrical element. This type of application is shown in FIG. 4.

The term 'rotationally symmetrical form' used here is by no means restricted to a particular form, but the rotationally symmetrical form may be, for example, a cylinder, ball, cone, circle or any combination of these.

The measurement window 2 made of an optical material and used in the disclosure is provided with at least one planar surface 7 through which light is arranged to be guided or reflected onto a measurement surface 2a of the measurement window 2 made of an optical material. The embodiment of FIGS. 4 and 5 has one measurement surface 2a. This is not, however, the only option but a plural number of measurement surfaces 2a may also be provided. The bundle of light beams is guided through the planar surface 7 to the measurement surface 2a as shown in FIG. 4. The travel of light in the window 2 made of an optical material is shown schematically in FIG. 4 by broken lines. The arrival of light from the light source to the planar surface 7 is shown schematically by an arrow 8a in FIG. 5. The bundle of light beams is guided from the light source as shown by the arrow 8a through an opening 9a to the planar surface 7 and the reflected light, correspondingly, through an opening 9b onwards for analysis. Openings 9a and 9b are placed so that they open at least partly to the sealing surface 3. The detail can be seen for example in FIG. 1. The light source is not presented in the figures. In FIG. 5 an arrow 8b shows schematically how light is guided for analysis from the window made of an optical material through the opening 9b. The means used for the analysis are not presented in the figures.

The planar surface 7 may be implemented so that light travels through the surface in question as shown in FIGS. 4 and 5. This is not, however, the only option but the planar surface 7 may also be implemented so that it functions as a reflective surface, in which case light is guided into the optical measurement window and inside the optical measurement window further to the planar surface 7 from where it is reflected towards the measurement surface 2a. This type of application is shown in FIGS. 6 to 10.

With regard to the light source and the means used in the analysis, we refer to the FI patent publications mentioned above, in which these have been discussed in greater detail.

In the examples of the figures, the measurement window made of an optical material is manufactured as a piece made of a uniform material. This is not, however, the only option but the measurement window made of an optical material may also be a combination of two separate parts. The separate parts may be attached together by gluing, for example. The joint surfaces should be of a good optical quality and the joint surface should be symmetrical with regard to incoming and outgoing light. The joint surface may be a planar, concave or convex surface. FIGS. 6 to 10 show an example of a measurement window made of separate parts. In the example of the figure the measurement window is made of two parts. It is also possible to use more than two parts. In FIGS. 6 to 10 like parts are indicated with like reference numerals as in FIGS. 1 to 5.

Figure 10:
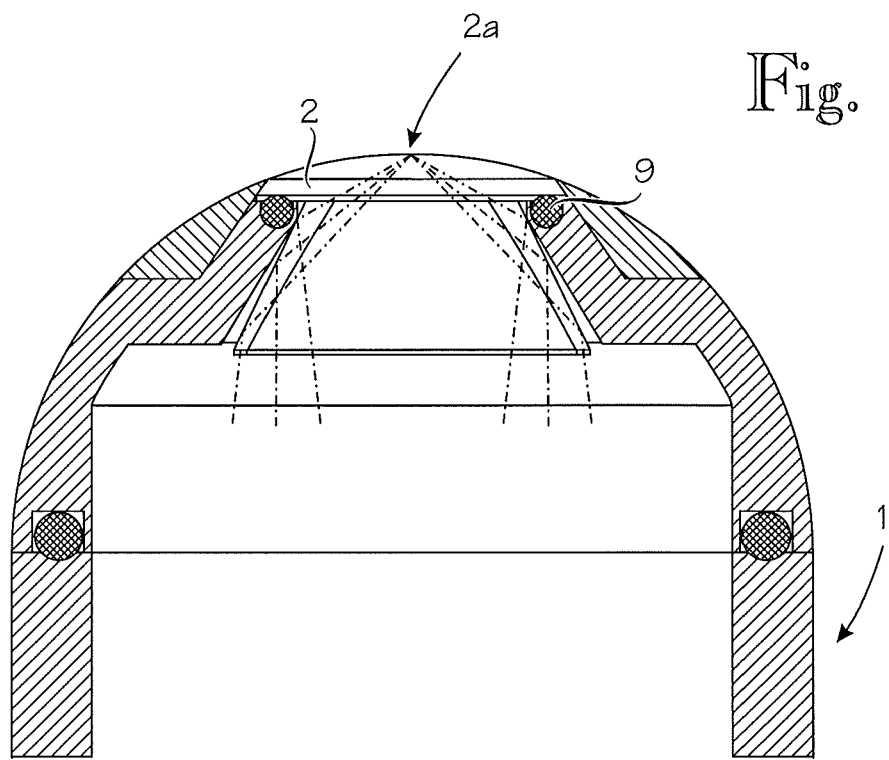

FIG. 10 also shows an implementation for providing a simple and affordable sealing of the measurement window made of an optical material. As stated above, an exemplary advantage of embodiments disclosed is that since the window made of an optical material can be installed from the process side and the sealing surfaces manufactured in the manner described above, the pressure prevailing in the process does not tend to open the sealing but presses the window made of an optical material tightly against the sealing surface provided in the frame structure. In that case, the sealing may be advantageously implemented by one seal, which may for example be a rotationally symmetrical seal, such as an O-ring. Such a rotationally symmetrical seal is indicated in FIG. 10 by reference numeral 8.

FIG. 10 also shows with broken lines how light beams travel to the measurement surface 2a and back for guidance to the analysis devices.

The exemplary embodiments disclosed herein do not restrict the invention but the various details of the disclosure may be fully freely modified within the scope of the claims.

Thus, it will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

What is claimed is:

1. A measurement window structure for an optical process measurement device, the measurement window structure comprising:
   a measurement window made of an optical material and having a measurement surface that is configured for placement into a process solution;
   a sealing surface for a frame structure of the optical process measurement device for facing the process solution, the measurement window being arranged to press against the sealing surface; and
   attaching means for pressing the measurement window against the sealing surface to attach the measurement window to the frame structure, the sealing surface being a rotationally symmetrical surface and the surface pressing against the sealing surface being a rotationally symmetrical surface, the surface of the measurement window pressing against the sealing surface being provided with at least one planar surface on the rotationally symmetrical surface through which light will be guided or reflected to the measurement surface, and the sealing surface being at least partly provided with an opening through which light will be guided to the planar surface.

2. A measurement window structure according to claim 1, wherein the sealing surface is at least partly provided with an opening through which light will be guided from the measurement window for analysis.

3. A measurement window structure according to claim 1, wherein the sealing surface of the measurement window is of a size equal to a largest dimension of the measurement window.

4. A measurement window structure according to claim 1, wherein the measurement window is a rotationally symmetrical element.

5. A measurement window structure of claim 1, wherein each rotationally symmetrical surface is formed as at least one of: a cylinder, a ball, a cone, a circle and a combination of these.

6. A measurement window structure according to claim 4, wherein the measurement window is formed of at least two separate parts attached together.

7. A measurement window structure according to claim 6, wherein the parts are attached together by gluing.

8. A measurement window structure according to claim 1, comprising: plural measurement surfaces.

9. An optical process measurement device comprising:
   a measurement window made of an optical material and having a measurement surface that is configured for placement into a process solution;
   a sealing surface for a frame structure of the optical process measurement device for facing the process solution, the measurement window being arranged to press against the sealing surface; and
   attaching means for pressing the measurement window against the sealing surface to attach the measurement window to the frame structure, the sealing surface being a rotationally symmetrical surface and the surface pressing against the sealing surface being a rotationally symmetrical surface, the surface of the measurement window pressing against the sealing surface being provided with at least one planar surface on the rotationally symmetrical surface through which light will be guided or reflected to the measurement surface, and the sealing surface being at least partly provided with an opening through which light will be guided to the planar surface.

* * * * *